United States Patent [19]
Fuxe

[11] 3,978,216
[45] Aug. 31, 1976

[54] METHOD FOR TREATING SCHIZOPHRENIA AND METHOD AND COMPOSITION FOR POTENTIATING NEUROLEPTIC DRUGS

[75] Inventor: Kjell Fuxe, Sollentuna, Sweden

[73] Assignee: Nelson Research & Development Company, Irvine, Calif.

[22] Filed: July 16, 1975

[21] Appl. No.: 596,571

Related U.S. Application Data

[63] Continuation-in-part of Ser. No. 475,856, June 3, 1974, Pat. No. 3,947,579.

[52] U.S. Cl. ............................... 424/247; 424/267; 424/274; 424/279; 424/319
[51] Int. Cl.[2] ................. A61K 31/54; A61K 31/195
[58] Field of Search ........................... 424/247, 319

[56] References Cited
UNITED STATES PATENTS
3,471,548   10/1969   Keberle ............................... 260/471

OTHER PUBLICATIONS
Medicinal Chemistry – Psychopharmacological Agents II (1967) pp. 106–108.

*Primary Examiner*—Stanley J. Friedman
*Attorney, Agent, or Firm*—Martin A. Voet

[57] ABSTRACT

A method for treating schizophrenia and a method and composition for potentiating the beneficial effects and reducing the side effects of neuroleptic drugs. Schizophrenia is treated with a GABA-like compound such as Lioresal. Neuroleptic drugs are potentiated by coadministering to a schizophrenic a neuroleptic drug and a GABA-like drug such as Lioresal.

2 Claims, No Drawings

METHOD FOR TREATING SCHIZOPHRENIA AND METHOD AND COMPOSITION FOR POTENTIATING NEUROLEPTIC DRUGS

RELATIONSHIP TO PRIOR APPLICATION

This application is a Continuation-in-Part of U.S. Ser. No. 475,856 filed June 3, 1974, now U.S. Pat. No. 3,947,579.

BACKGROUND OF THE INVENTION

Background of the Prior Art

U.S. Pat. No. 3,471,548 describes compounds having the structural formula

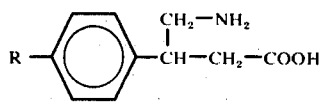

wherein R is chloro, bromo, fluoro or fluoromethyl. The compounds are known to cross the blood brain barrier and are known to have muscle relaxant properties and to be useful in the treatment in man of spasticity of spinal origin.

Neuroleptic drugs are used to treat schizophrenia. Examples of common neuroleptic drugs include phenothiazines such as chloropromazine; butyrophenones such as haloperidol and others such as pimocide and clozapine. Side effects of neuroleptic drugs include sedation and tardive dyskinesias. The latter side effect is particularly important because it results in involuntary muscle movements especially of the face and mouth which become irreversible. The onset of this side effect is directly related to the amounts of and length of time which a neuroleptic drug is used in treatment.

SUMMARY OF THE INVENTION

There has now been discovered a method for treating schizophrenia and a method and composition for potentiating the beneficial effects and for reducing the side effects of neuroleptic drugs.

The foregoing results are obtained by administering to a schizophrenic an effective amount of a gabergic compound or by coadministering to a schizophrenic a neuroleptic drug and a potentiating amount of a gabergic compound such as γ-hydroxybutyrolactone, γ-hydroxybutyrate, aminooxyacetic acid, 5-ethyl-5-phenyl-2-pyrrolidone, 1-hydroxy3-amino-2-pyrrolidone, or a compound having the structural formula

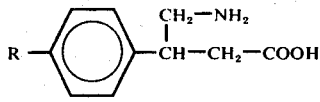

wherein R is halogen or trifluoromethyl and salts thereof.

The present invention further relates to a composition comprising a neuroleptic drug and a potentiating amount of a gabergic compound together with a suitable pharmaceutical carrier.

DETAILED DESCRIPTION OF THE INVENTION

Compounds having the foregoing structural formula such as, for example, β-(4-chlorophenyl)-γ-aminobutyric acid and pharmaceutically acceptable salts thereof and pharmaceutical compositions thereof and their manner of making is described in U.S. Pat. No. 3,471,548 and relevant portions thereof are hereby incorporated by this reference. γ-hydroxybutyrolactone, γ-hydroxybutyrate and aminooxyacetic acid, 5-ethyl-5-phenyl-2-pyrrolidone, 1-hydroxy-3-amino-2-pyrrolidone are also known to those of skill in the art.

The amount of GABA-like or gabergic compound which may be used in the present invention ranges from about 0.1 to about 100 mg/kg and preferably from about 0.1 to about 10 mg/kg and preferably about 0.1 to 1.5 mg/kg per day.

The term "gabergic" compound herein refers to compounds which are related pharmacologically to γ-aminobutyric acid, known as GABA. Typical examples of GABA-like or gabergic compounds include γ-hydroxybutyrolactone, γ-hydroxybutyrate, aminooxyacetic acid, 5-ethyl-5-phenyl-2-pyrrolidone, 1-hydroxy-3-amino-2-pyrrolidone, and β-(4-chlorophenyl)-γ-aminobutyric acid. When used herein, the term "gabergic compound" refers to any gabergic compound, such as, but not limited to, the foregoing gabergic compounds.

Neuroleptic drugs which may be used in the present invention include phenothiazine derivatives such as chlorpromazine, promozine, triflupromozine, acetophenazine, butaperazine, corphenazine, fluphenazine, perphenazine, prochloroperazine, thiopropazate, trifluoperazine, mepazine, mesoridazine, piperacetazine, thioridazine, chloroprothizine, thiothixine, benzoctamine, cidorepin, clomacran. clopenthixol, clothiapine, clothixamide, clozapine, dimeprozan, doxepin, lovapine, perlapine and pinovepin; rauwolfia derivatives including deserpidine, metaserpate, rescinnamine, reserpine, bezquinamide, oxypertine, tetrabenazine, indopine, indriline, methopholine, milipertine, molindone, solypertine, yohimbine and solertine; diphenylmethane derivatives including benactyzine, piperilate, azacyclonal, captodiamine, hydroxyzine, cyprolidol, hexandrol and pimizide; and butyrophenone derivatives including haloanisone, haloperidol, oxaperone, benperidal, carperone, droperidal, fluspirilene, meperone, penfluridol, pipamperone, seperidol, spiperone and trifluperidol. When used herein, the term "neuroleptic drugs" refers to any neuroleptic drug such as, but not limited to, the foregoing neuroleptic drugs.

While Applicant does not necessarily rely on the following theory of action as to why the gabergic compounds are useful in the treatment of schizophrenia and to potentiate the effects of neuroleptic drugs, Applicant believes that known neuroleptic drugs act by blocking dopamine receptor activity in the brain. However, whenever the dopamine receptor activity is blocked, compensatory mechanisms are initiated by the central nervous systems to restore normal dopamine receptor activity. The compensatory mechanisms act by blocking the normal inhibitory γ-aminobutyric acid (GABA) activity of dopamine cell bodies, thus tending to increase dopamine neuron activity. Applicant believes the gabergic compounds selectively interfere with the compensatory mechanisms controlling activity in the mesolimbic dopamine neurons by increasing GABA receptor activity in the medial dopamine cell bodies of the midbrain, which inervate the limbic forebrain and thereby potentiate the effect of neuroleptic drugs by blocking the the increase of limbic dopamine turnover otherwise caused by the neuroleptic drug. In this manner, the gabergic compound can be used to potentiate the beneficial effects of neuroleptic drugs, since their antipsychotic effect is believed to be due to blockade of limbic dopamine receptors and themselves have therapeutic benefit in the treatment of schizophrenia. Applicant further believes that extrapyramidal side effects, e.g., tardive dyskinesia and parkinsonian-like side effects, are mediated through the blockade of neostriatal dopamine receptors. Thus, when coadministered with the foregoing neuroleptic drugs, the gabergic compounds described herein allow the use of lower doses of neuroleptic drugs to obtain the same antipsychotic effect as obtained with higher doses of neuroleptic drug without the gabergic compounds. At the same time, neostriatal dopamine receptor blockade is reduced and thus extrapyramidal side effects are likewise reduced or eliminated. As a result of the foregoing, the dose of neuroleptics now given may be decreased by a factor of 2–20 times (about 5–50% of usual dose) when co-administered with an effective amount of one of the gabergic compounds of the present invention.

For purposes of this invention, the term "co-administered" means the administration of a neuroleptic drug and a gabergic compound as described herein to a patient during a course of treatment.

For purposes of this disclosure, the phrase "treatment of schizophrenia" means the temporary alleviation of at least some of the signs or symptoms of schizophrenia.

The pharmaceutical compositions may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tables. These excipients may be, for example, inert diluents, for example calcium carbonate, sodium carbonate, lactose, calcium phosphate or sodium phosphate; granulating and disintegrating agents for example, maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with an oil medium, for example, arachis oil, liquid paraffin or olive oil.

Aqueous suspensions contain the active ingredients in admixture with excipients suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example polyoxyethylene sorbitol monooleate, or condensation product of ethylene oxide with partial ester derived from fatty acids and hexitol anhydrides, for example polyoxyethylene sorbitan monooleate. The said aqueous suspensions may also contain one or more preservatives, for example, ethyl, or n-propyl, p-hydroxy benzoate, one or more coloring agents, one or more flavoring agents and one of more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients for example, sweetening, flavoring and coloring agents, may also be present.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile, injectable preparation, for example as a sterile, injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol.

The pharmaceutical compositions may b tableted or otherwise formulated so that for every 100 parts by weight of the composition there are present between 5 and 95 parts by weight of the active ingredients and preferably between 25 and 85 parts by weight of the active ingredients. The dosage unit form will generaly contain between about 10 mg and about 500 mg of the active ingredients. A preferred dosage rate for oral administration is of the order of 1–1000 mg daily, optionally in divided doses.

From this foregoing formulation discussion, it it apparent that the compositions of this invention can be administered orally or parenterally. The term "parenteral" as used herein includes subcutaneous injection, intravenous, intramuscular, or intrasternal injection or infusion techniques.

This invention is further demonstrated by the following examples in which all parts are by weight.

EXAMPLE I

The effect of β-(4-chlorophenyl)-γ-aminobutyric acid Lioresal) on the pimozide-induced increase in dopamine fluorescence disappearance from the neostriatum and subcortical limbic areas of rats after treatment with α-methyltyrosine methyl ester.

Dopamine neuron nerve endings can be made to fluoresce strongly as a result of the presence of stored dopamine. These stores of dopamine are not static; there is a continual release, reuptake, degradation and de novo synthesis at the nerve ending.

α-methyltyrosine methyl ester is an inhibitor of dopamine synthesis. Fluorescence microscopy shows that α-methyltyrosine methyl ester depletes dopamine stores. Therefore, α-methyltyrosine methyl ester may be used to determine dopamine turnover in the nerve endings since turnover is directly proportional to the rate of dopamine depletion.

When dopamine receptors are blocked by drugs such as pimozide and haloperidol, the dynamic state of dopamine at and in the nerve endings increase. This appears as an increased disappearance of fluorescence after administration of α-methyltyrosine methyl ester. This increase results from a compensatory response to the decreased stimulation of the nerve cells normally receiving the dopamine stimulation.

α-methyltyrosine methyl ester (H 44/68), an inhibitor of dopamine synthesis, was given to male Sprague-Dawley rats i.p. in a dose of 250 mg/kg 4 hrs before killing. β-(4-chlorophenyl)-γ-aminobutyric acid (Lioresal) was given i.p. in a dose of 10, 20 or 25 mg/kg 15 minutes before H 44/68. Pimozide was given i.p. in a dose of 1 mg/kg 2 hours before H 44/68, and haloperidol in a dose of 5 mg/kg 1 hours before H 44/68. The dopamine levels were determined by measuring histochemical fluorescence. The fluorescence intensity reflects the amount of dopamine present. The fluorescence intensity was semi-quantitatively estimated on coded slides. 3 = strong; 2 = moderate; 1 = weak; ½ = very weak. Number of animals is shown within parenthesis. Table 1 below tabulates the data obtained.

Table 1

| Treatment | Fluorescence intensity | | | | | |
|---|---|---|---|---|---|---|
| | Neostriatum | | | Limbic forebrain | | |
| No drug treatment | 3 (4) | | | 3 (4) | | |
| H44/68 | 0.5(1) | 1(2) | 1.5(2) | 0.5(2) | 1(2) | 1.5(1) |
| Pimozide + H44/68 | 0(7) | 0.5(1) | | 0 (7) | 0.5(5)$^d$ | |
| Pimozide + Lioresal (20) + H44/68 | 0(2) 0.5(4) | 1.5(2) | 2(2) | 1.5(4) | 2(6)$^e$ | |
| Pimozide + Lioresal (10) + H44/68 | 0(3) 0.5(3) | 1 (2) | 1.5(3) | 1(1) | 1.5(6) | 2(4)$^f$ |
| Haloperidol + H44/68 | 0.5(1) | 1(6) | | 0.5(2) | 1(6)$^g$ | |
| Haloperidol + Lioresal (10) + H44/68 | 1(4) | 1.5(2) | 2(1) | 2(6) | 2.5(2)$^h$ | |
| Lioresal (25) + H44/68 | 1(1) | 1.5(3) | | 1(1) | 1.5(1) | 2(2) |
| Lioresal (10) + H44/68 | 1.5(2) | 2(1) | | 1.5(1) | 2(1) | 2.5(1) |

Statistical significance according to Tukey's Quick test:

| | | | |
|---|---|---|---|
| d–e: | p < 0.001 | g–h: | p < 0.001 |
| d–f: | p < 0.001 | | |

The foregoing Example I shows that the dopamine turnover at the nerve endings is increased by pimozide and haloperidol. This increase is antagonized by β-(4-chlorophenyl)-γ-aminobutyric acid in the limbic forebrain (nuc. accumbens, tuberculum olfactorium). Thus, as seen from the foregoing table, the increased disappearance (i.e. decrease in amount) of dopamine fluorescence from the limbic forebrain but not from the neostriatum seen after introduction of pimozide and haloperidol is significantly counteracted by pre-treatment with β-(4-chlorophenyl)-γ-aminobutyric acid.

It can thus also be stated that Lioresal can counteract the pimozide increase in dopamine turnover also in the limbic cortex. This is important, since thought processes are usually linked to cortical regions and therefore these limbic dopamine receptors may be particularly involved in the control of the abnormal thought processes found in schizophrenia.

EXAMPLE II

Effect of γ-OH-butyrolactone on the pimozide-induced increase in DA fluorescence disappearance found after treatment with α-methyl tyrosine methyl ester in rats (6–9).

The method used in Example I was followed. Pimozide was given i.p. in a dose of 1 mg/kg 2 hrs before α-methyl tyrosine methyl ester (H44/68) (250 mg/kg, i.p., 2 hr). γ-OH-Butyrolactone was given i.p. 15 min. before H44/68 in a dose of 300 mg/kg. The results of the study showed that γ-hydroxybutyrolactone selectively counteracted the pimozide-induced increases in dopamine turnover in the limbic system.

Thus, the foregoing Example II shows that γ-hydroxybutyrolactone also potentiates the antipsychotic action of neuroletpic drugs and at the same time reduces extrapyramidal-like side effects of neuroleptic drugs by enabling a lowering of the dosage of the neuroleptic given. The study also showed that γ-hydroxybutyrolactone would also be useful alone in the treatment of schizophrenia.

EXAMPLE III

Effect of Lioresal and aminooxyacetic acid (AOAA) on the pimozide-induced increase in dopamine fluorescence disappearance found after treatment with α-methyl tyrosine methyl ester in rats (9–10).

The method of Example I was followed, pimozide (1 mg/kg i.p. was given 2 hrs before α-methyl tyrosine methyl ester (250 mg/kg, i.p. 2 hr before filling). Lioresal (5 mg/kg, i.p.) was given 15 min. before α-methyl tyrosine methyl ester, as was aminooxyacetic acid (25 mg/kg, i.p.).

The results of the study showed that aminooxyacetic acid selectively counteracted the pimozide-induced increase in dopamine turnover in the limbic system (nuc. accumbens, tuberculum olfactorium)

Thus, the foregoing Example III also shows that aminooxyacetic acid potentiates the antipsychotic action of neuroleptic drugs and at the same time lowers extrapyramidal side effects by enabling a lowering of the dosage of the neuroleptic given. The study also shows that aminooxyacetic acid would also be useful alone in the treatment of schizophrenia.

EXAMPLE IV

Effect of 5-ethyl-5-phenyl-pyrrolidone (EPP) on the α-methyl tyrosine methyl ester induced dopamine fuorescence disappearance in the nuc. caudatus, nuc. accumbens and tuberculum olfactorium of rats.

The method of Example I was followed. EPP was given i.p. in a dose of 50 mg/kg 15 min. before α-methyl tyrosine methyl ester (H44/68) (250 mg/kg, i.p. 2 hr. before killing). The specific DA flourescense is given in arbitrary fluorescence units. A Leitz microspectrofluorometer was used. The number of animals used is shown within parenthesis. The data is reported as a mean ± s.e.m. in Table 2 below.

Table 2

| Treatment | Dopamine fluorescence | | | | | |
|---|---|---|---|---|---|---|
| | Tuberculum olfactorium | % | nuc. accumbens | % | nuc. caudatus | % |
| No drug treatment | 30.9 ± 1.8 (3) | 100 | 52.3 ± 4.9 (3) | 100 | 25.3 ± 1.3 (3) | 100 |
| H44/68 | 18.1 ± 1.5 (5) | 58 | 29.8 ± 1.4 (5) | 57 | 13.7 ± 0.8 (5) | 54 |
| EPP (50) + H44/68 | 28.7 ± 1.6 (4) | 93 | 37.1 ± 1.2 (5) | 71 | 14.4 ± 1.3 (5) | 57 |

EXAMPLE V

The effect of Lioresal, aminooxyacetic acid (AOAA) and 5-ethyl-5-phenyl-2-pyrrolidone (EPP) on the pimozide induced increase of dopamine turnover in the dopamine terminal islands of the entorhinal cortex.

The method used in Example I was followed. Lioresal (10 mg/kg, i.p.), EPP (200 mg/kg, i.p.) and AOAA (25 mg/kg, i.p.) were administered 15 min. and 2 hr. (AOAA) before the α-methyl tyrosine methyl ester (H44/68) injection (250 mg/kg, i.p. 1 hr before killing). Pimozide (1 mg/kg) was given i.p. 2 hrs before the H44/68 injection.

The results of this study indicated that both EPP and AOAA, like Lioresal, counteracted the pimozide-induced increase in dopamine turnover in the entorhinal cortex. These results indicated that AOAA and EPP can selectively counteract the pimozide-induced increase in dopamine turnover in the limbic system including the important limbic cortical region.

Thus, the foregoing study shows that gabergic drugs of the EPP type also can potentiate the antipsychotic action of neuroleptic drugs, and also be active as such in schizophrenia. At the same time, extrapyramidal side effects of neuroleptic drugs are reduced by gabergic drugs since they enable a lowering of dosage of the neuroleptic drug given.

EXAMPLE VI

Tablets, each containing 60 mg of the active combination can be prepared, for example, from the following ingredients:

| | Mg. |
|---|---|
| β-(4-chlorophenyl)-γ-aminobutyric acid | 40 |
| Lactose | 95 |
| Wheat starch | 54 |
| Gelatine | 6 |
| Arrowroot | 24 |
| Stearic acid | 6 |
| Talcum | 15 |
| Chlorpromazine | 10 |
| | 250 |

Preparation of the tablets — The active ingredients are homogeneously mixed with lactose and wheat starch and pressed through a 0.5 mm mesh sieve. Gelatine is dissolved in 10 times its own weight of water; the powder mixture is evenly moistened with this solution and kneaded until a plastic mass has formed which is then pressed through a 3 mm mesh sieve, dried at 45°C and then sifted through a 1.5 mm mesh sieve. Arrowroot, stearic acid and talcum are finely sifted and worked into the resulting mixture, and the paste is then made up in the usual manner into tablets of 9 mm diameter and 250 mg weight.

EXAMPLE VII

Example VI is repeated, except a number of tablet formulations were prepared using one of the following compounds in the place of β-(4-chlorophenyl)-γ-aminobutyric acid: γ-hydroxybutyrolactone, γ-hydroxybutyrate, aminooxyacetic acid, 5-ethyl-5-phenyl-2-pyrrolidone and 1-hydroxy-3-amino-2-pyrrolidone; and one of the following neuroleptic compounds in the place of chlorpromazine: fluphenazine, clozapine, resperpine and haloperidol.

I claim:

1. A method for potentiating the neuroleptic activity of phenothiazine derivatives having neuroleptic activity comprising administering to a schizophrenic about 5 to about 50 percent of a conventional dosage amount of a phenothiazine derivative having neuroleptic activity and an amount equal to about 0.1 to about 100 mg/kg of aminooxyacetic acid or a pharmaceutically acceptable salt thereof.

2. A method for potentiating the neuroleptic activity of phenothiazine derivatives comprising administering to a schizophrenic about 5 to about 50 percent of a conventional dosage amount of a phenothiazine derivative selected from the group consisting of chlorpromazine and theoridazine and an amount equal to about 0.1 to about 10 mg/kg of aminooxyacetic acid or a pharmaceutically acceptable salt thereof.

* * * * *